United States Patent [19]

Keyser

[11] 4,246,914

[45] Jan. 27, 1981

[54] ABRASIVE RELIEF DEVICE FOR THE FOOT

[76] Inventor: Earl W. Keyser, Rte. 1, Box 629, Mount Shasta, Calif. 96067

[21] Appl. No.: 2,543

[22] Filed: Jan. 10, 1979

[51] Int. Cl.³ ............................................. A45D 29/20
[52] U.S. Cl. .................................................. 132/76.4
[58] Field of Search .................. 132/76.4, 73, 76.2, 132/76.4, 76.5, ; 128/69, 25 B, 60, 62 R, 555, 582, 800; 524/36; 272/96

[56] References Cited

U.S. PATENT DOCUMENTS

| | | | |
|---|---|---|---|
| 1,172,089 | 2/1916 | Wild | 132/76.4 |
| 1,829,338 | 10/1931 | Bynum | 132/76.5 |
| 2,735,434 | 2/1956 | DeRossett | 132/76.4 |
| 3,198,198 | 8/1965 | Bittner | 132/76.4 |
| 3,865,122 | 2/1975 | Dabbs | 132/73 |

*Primary Examiner*—G. E. McNeill
*Attorney, Agent, or Firm*—Erik M. Arnhem

[57] ABSTRACT

A bar defining a flat base and a surface having a longitudinal flat center section merging bilaterally into curved sections which extend to the edges of the base, the surface of the bar is divided into an abrasive and a non-abrasive portion.

1 Claim, 3 Drawing Figures

ABRASIVE RELIEF DEVICE FOR THE FOOT

Field of the Invention:

(1) Background of the Invention:

The invention relates to a partially abrasive bar or board, adapted to remove callouses, corns and the like from one tired foot while the other foot is accommodated supportively adjacent the abraded portion of the bar. When a foot is applied properly and as directed to the bar, according to the invention, it will remove corns, dead flesh or other hardenings, developed on the undersurface of and afford immediate relief to an aching foot.

The appearance of corn and callouses on the foot is a recurring problem, in particular with respect to feet having been subjected to prolonged friction and pressure.

The presently used medicated pads, or other devices for removal of such hardenings of the skin do not give prompt or adequate relief to the feet, or cannot be considered expedient tools usable for the above stated purpose.

(2) Description of Prior Art

The following U.S. patents are believed to be the art most pertinent to my invention, and, directed to class 128, subclasses 25-B and 62 and class 132, subclass 76.4:
U.S. Pat. No. 1,664,664—Crum—1928; U.S. Pat. No. 2,079,311—Blumenthal—1937; U.S. Pat. No. 2,082,829—Gerlofson—1937; U.S. Pat. No. 2,400,023—Potter—1946; U.S. Pat. No. 2,468,327—Hartung—1949; U.S. Pat. No. 2,735,434—Rossett—1958

Crum, Blumenthal, Gerlofson, and Hartung disclose exercising devices, for persons in standing position.

Potter is a boot used as a massaging device.

Rossett shows a recessed platform for two abraded vertically directed members.

None of the above cited patents discloses a device as simply constituted as mine, intended for effective removal of corns, etc., by a person primarily in a sitting position.

SUMMARY OF THE INVENTION

It is, therefore an object of the invention to provide a simple, inexpensive, but effective relief device for quick removal of excess skin or flesh, accumulated under the foot.

It is a further object of the invention to provide means, incorporated in the device, according to the invention, for pedal support during its use.

In addition to the information stated under (c), (e) and (f) above, my invention is so shaped that it affords relief to the various anatomical parts of the foot undersurface, such as, the instep, heel, and palm. The abraded surface of my device, according to the invention, serves the dual purposes of removing dead skin, horny formations, etc. under the foot and to stimulate its blood circulation.

Figure 1:
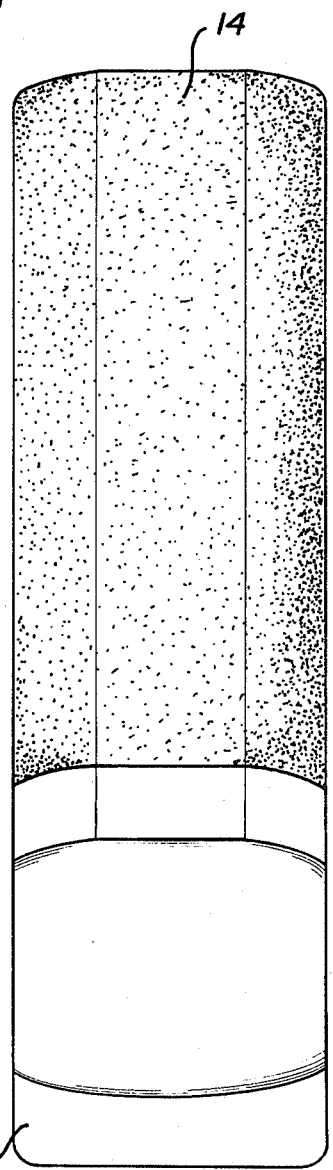
FIG. 1 illustrates a top view of a bar, according to the invention.

DESCRIPTION OF THE PREFERRED EMBODIMENT:

In the drawings like reference characters designate similar parts in the several views.

Figure 3:
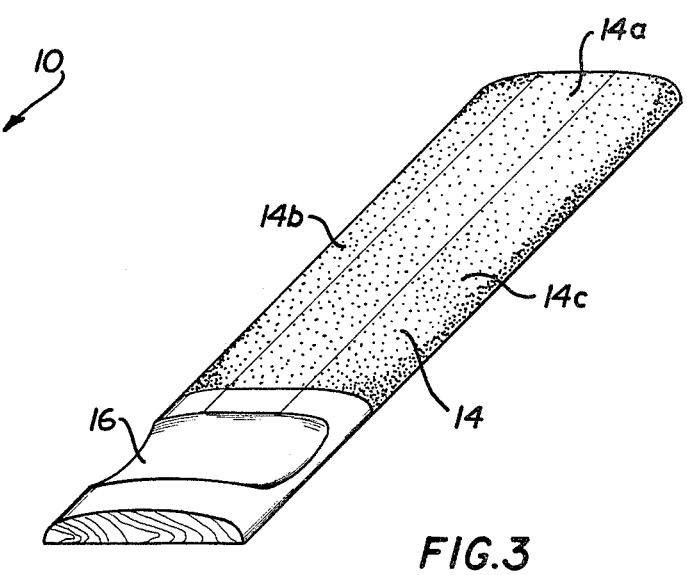
FIG. 3 shows a perspective view of the bar in FIG. 1.
Figure 2:
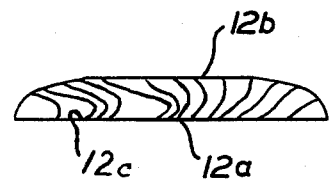
FIG. 2 is cross sectional view of the bar, taken on line 2—2 of FIG. 1.

Referring now in detail to the drawings, numeral 10 designates the bar, as illustrated in FIG. 1, constituting one integral piece, preferably made of wood, plastic, or the like; it has a flat base 12a, as shown in FIG. 2, for placement on a floor, ground, etc. The surface 12b of the bar 10 is divided into an abraded, respectively substantially smooth surface 14 and 16. The abraded surface 14 may be produced by grooves or tiny projections made therein, or, preferably by coating or covering same with coarse sand or paper, which may be glued on surface 12b of the bar. As illustrated in FIG. 3, the surface 12b of bar 10 is basically divided into three longitudinal sections (indicated by solid lines), i.e. a substantially flat center section 14a, which bilaterally extend smoothly into two curved portions 14b, 14c merging with the lateral edges 12c of base 12a.

Surface 16 of bar 10 is appropriately of a shorter length than surface 14 and may optionally be provided with a depression as indicated in FIG. 1, accommodating one foot supportively, while the other one is treated on the abraded surface 14.

In use bar 10 is placed horizontally, e.g., on the floor, vis-a-vis the seated user, who places his right foot firmly and supportively on surface 16 (when placed to the right of user) so that bar 10 will remain stationary on the floor. He then draws his left foot (as often as is required for the above stated purpose), across the abraded surface 14 towards himself; the flat center portion 14a thereof is intended for treatment of the foot instep (arched middle portion), and also the heel, palm and toe sections of the foot, which, when drawn with adequately applied pedal pressure across surface 14, will be relieved of callouses, corns, dead skin, etc. developed under the foot sole. This treatment will render instant relief to a tired and aching foot. When the treatment of one foot has been completed, bar 10 is simply turned around for treatment of the other foot.

The preferred dimensions of the bar, according to the invention, are as follows:

Width: 2½", of which center section 14a (FIG. 3) measures 1¼ inch.

Length: 13¼ inches of which surface 14 covers approximately 9 inches, and surface 16, 4½ inch.

Sections 14b, c of bar 10 extend curvedly to base edges 12c, to facilitate the drawing of the foot across the abraded surface 14 (eliminating any sharp edges that may hurt the foot) and also to facilitate the application of sand paper (if used for the purpose) across portion of surface 12b of bar 10 clear around to edges 12c of its base 12a.

While the foregoing has illustrated and described what is now contemplated to be the best mode of carrying out the invention, same is, of course, subject to modifications without departing from the spirit and scope of invention.

Therefore, it is not desired to restrict the invention to the particular constructions illustrated and described, but to cover all modifications, that may fall within the scope of the appended claims.

I claim:

1. In a relief device for the foot, comprising one elongated bar, having an abraded surface including a longitudinal substantially flat center section merging bilaterally therefrom into curved sections, and a non-abraded surface, extending in alignment with the abraded surface, for supportive accommodation of the other foot, while the foot is treated on the abraded surface of the bar.

* * * * *